United States Patent [19]
Eriksson et al.

[11] Patent Number: 5,686,428
[45] Date of Patent: Nov. 11, 1997

[54] PHARMACEUTICAL COMPOSITION

[75] Inventors: Bertil F. H. Eriksson, Tumba, Sweden; Raymond F. Schinazi, Decatur, Ga.

[73] Assignee: Aktiebolaget Astra, Sodertalje, Sweden

[21] Appl. No.: 192,061

[22] Filed: Feb. 4, 1994

Related U.S. Application Data

[63] Continuation of Ser. No. 33,852, Mar. 19, 1993, abandoned, which is a continuation of Ser. No. 764,983, Sep. 23, 1991, abandoned, which is a continuation of Ser. No. 335,216, Apr. 7, 1989, abandoned.

[51] Int. Cl.$^6$ .................... A61K 31/70; A61K 31/66
[52] U.S. Cl. .................... 514/50; 514/51; 514/120
[58] Field of Search .................... 514/50, 51, 120

[56] References Cited

U.S. PATENT DOCUMENTS

| | | | |
|---|---|---|---|
| 4,724,232 | 2/1988 | Rideout et al. | 514/50 |
| 4,857,511 | 8/1989 | Rideout et al. | 514/50 |

FOREIGN PATENT DOCUMENTS

| | | | |
|---|---|---|---|
| 0594223 | 4/1991 | European Pat. Off. | |

OTHER PUBLICATIONS

Bertil F. H. Eriksson and Raymond F. Schinazi, Combinations of 3'-Azido-3'-Deoxythymidine (Zidoundine) . . . Antimicrobial Agents & Chemotherapy, vol. 33, No. 5, pp. 663–669, (May 1989).

Eriksson, B.G., et al., "Inhibition of Reverse Transcriptase Activity of Avian Myeloblastosis Virus by Pyrophosphate Analogues", Antiviral Res., 2:81–95 (1982).

Eriksson, B., et al., "Different Patterns of Inhibition of Avian Myeloblastosis Virus Reverse Transcriptase Activity by 3'-Azido-3'-Deoxythymidine-5'-Triphosphate and its thero Isomer," Antimicrob. Agents Chemother., 31:(1987) 600–604.

Farthing, C., et al., "Treatment of Cytomegalovirus Pneumonitis with Foscarnet (Trisodium Phosphonoformate) in Patients with AIDS," J. Med. Virol. 22:157–162 (1987).

Farthing, C.F., et al., "Phosphonoformate (Foscarnet): A Pilot Study in AIDS and AIDS Related Complex," AIDS 1: (1987) 21–25.

Field, A.K., et al., "'The End of Innocence' Revisited: Resistance of Herpesviruses to Antiviral Drugs," Clin. Microb., Rev. 7: (1964) 1–13.

Fischer, A.G., et al., "Biologically Diverse Molecular Variants within a Single HIV-1 Isolate," Nature, 334:444–447 (1988).

Fischl, M.A., et al., "The Efficacy of Azidothymidine (AZT) in the Treatment of Patients with AIDS and AIDS–Related Complex. A Double–Blind, Placebo–Controlled Trial," New Engl. J. Med., 317:185–191 (1987).

Fletcher, C.V., et al., "Foscarent for the Suppression of Human Immunodeficiency Virus Replication," Antimicrob. Agents Chemother., 38: (1994) 604–607.

Frank, K.B., et al., "Mutually Exclusive Inhibition of Herpesvirus DNA Polymerase by Aphidicolin, Phosphonoformate, and Acyclic Nucleoside Triphosphates," Antimicrob. Agents Chemother. 27:445–448 (1985).

Furman, P.A., et al., "Phosphorylation of 3'-Azido-3'-Deoxythymidine and Selective Interaction of the 5'-Triphosphate with Human Immunodeficiency Virus Reverse Transcriptase," Proc. Natl. Acad. Sci. USA 83:8333–8337 (1986).

Gaub, J., et al., "The Effect of Foscarnet (Phosphonoformate) on Human Immunodeficiency Virus Isolation, T–Cell Subsets and Lymphocyte Function in AIDS Patients," AIDS 1:1 27–33 (1987).

Hall, M.J., et al., "Antiviral Drugs and Interferon Combinations," pp. 29–84 in J.H. Field (ed.) Antiviral Agents: The Development and Assessment of Antiviral Chemotherapy vol. II, CRC Press, Inc., Boca Raton, Florida (1988).

Hammer, S.H., et al., "Synergistic Activity of Granulocytemacrophase Colony–Simulating Factor and 3'-Azido-3'-Deoxythymidine Against Human Immunodeficiency Virus in vitro," Antimicrob. Agents Chemother. 31:1046–1050 (1987).

Hartshorn, K.L., et al., "Synergistic Inhibition of Human T–Cell Lymphotrophic Virus Type III Replication in vitro by Phosphonoformate and Recombinant α–A Interferon," Antimicrob. Agents Chemother. 31: 168–172 (1987).

Hartshorn, K.L., et al., Antimicrob. Agents Chemother. 30:189–191 (1987).

Hirsch, M.S., et al., "Treatment of Human Immunodeficiency Virus Infection," Antimicrob. Agents Chemother. 31: 839–843 (1987).

Hoffman, A.D., et al.; "Characterization of the AIDS–Associated Retrovirus Reverse Transcriptase and Optimal Conditions for its Detection in virons," Virology, 147: 326–335 (1985).

Hwang, B.C., et al., "A Point Mutation within a Conserved Region of the Herpes Simplex Virus DNA Polymerase Gene Confers Drug Resistance," J. Virol., 66: (1992) 1774–1776.

Im, G.J., et al., "Identification of the Amino Acid in the Human Immunodeficiency Virus Type 1 Reverse Transcriptase Involved in the Pyrophosphate Binding of Antiviral Nucleoside Triphosphate Analogs and Phosphonoformate. Implications for Multiple Drug Resistance," Biochem. Pharmacol., 46: (1993) 2307–13.

Jackson, J.B., et al., "Rapid and Sensitive Viral Culture Method for Human Immunodeficiency Virus Type 1," J. Clin. Micro 26: (1988) 1416–1418.

(List continued on next page.)

Primary Examiner—Jerome D. Goldberg
Attorney, Agent, or Firm—Dimitrios T. Drivas; John Scheibeler; Sherry M. Knowles

[57] ABSTRACT

Combinations of 3'-azido-3'deoxythymidine and phsphonoformate have been found to produce a synergistic inhibitory effect against human immunodeficiency virus (HIV).

3 Claims, 2 Drawing Sheets

OTHER PUBLICATIONS

Jacobo–Molina, A., et al., "Crystal Structure of Human Immunodeficiency Virus Type 1 Reverse Transcriptase Complexed with Double–Strand DNA at 3.0 A resolution shows bent DNA," *Proc. Natl. Acad. Sci. USA*, 90: (1993) 6320–6324.

Jacobson, M.A., et al., "Effect of Foscarnet Therapy on Infection with Human Immunodeficiency Virus in Patients with AIDS," *J. Infect. Dis.*, 158: (1988) 862–865.

Japour, A.J., et al., "Standardized Peripheral Blood Mononuclear Cell Culture Assay for Determination of Drug Susceptibilities of Clinical Human Immunodeficiency Virus Type 1 Isolates," *Antimicrob. Agents Chemother.* 37: (1993) 1095–01.

Klintmalm, G., et al., "Intravenous Foscarnet for the Treatment of Severe Cytomegalovirus Infection in Allograft Recipients," *Scand. J. Infec. Dis.* 17: 157–163 (1985).

Knox, K.K., et al., "Cytomegalovirus Isolate Resistant to Ganciclovir and Foscarnet from a Marrow Transplant Patient," *Lancet*, ii: (1991) 1292–1293.

Larder, B.A., "3'–Azido–3'–Deoxythymidine Resistance Suppressed by a Mutation Conferring Human Immunodeficiency Virus Type 1 Resistance to Nonnucleoside Reverse Transcriptase Inhibitors," *Antimicrob. Agents Chemother.*, 36: (1992) 2664–2669.

Larder, B.A., et al., "Susceptibilities of Zidovudine–Susceptible and –Resistant Human Immunodeficiency Virus Isolates to Antiviral Agents Determined by Using a Quantitative Plaque Reduction Assay," *Antimicrob. Agents Chemother.*, 34: (1990) 436–441.

Larder, BA, et al., "Site–Specific Mutagenesis of AIDS Virus Reverse Transcriptase," *Nature*, 327: (1987) 716–7.

Larder, B.A., et al., "Infectious Potential of Human Immunodeficiency Virus Type 1 Reverse Transcriptase Mutants with Altered Inhibitor Sensitivity," *Proc. Natl. Acad. Sci. USA*, 86: (1989) 4803–7.

Larder, B.A., et al., "HIV with Reduced Sensitive to Zidovudine (AZT) Isolated During Prolonged Therapy," *Science*, 243: 1731–1734 (1989).

Laskin, O.L., et al., "Ganciclovir for the Treatment and Suppression of Serious Infections Caused by Cytamegalovirus," *Am. J. Med.*, 83:201–207 (1987).

Lin, T., et al., "Synthesis and Biological Activity of Several Amino Analogues of Thymidine," *J. Med. Chem.* 21:109–112 (1978).

Lowe, D.M., et al., "Mutational Analysis of Two Conversed Sequence Motifs in HIV–1 Reverse Transcriptase," *FEBS Letters*, 282: (1991) 231–234.

Mayers, D.L., et al., "Characterization of HIV Isolates Arising After Prolonged Zidovudine Therapy," *J. Acquir. Immune Defic. Syndr.* 5: (1992) 749–759.

Mellors, J.W., et al., "A Single Conservative Amino Acid Substitution in the Reverse Transcriptase of Human Immunodeficiency Virus–1 Confers Resistance to (+)–(5S)–4,5,6, 7–tetrahydro–5–methyl–6(3–methyl–2–butenyl)imidazo[4,5,1–jk][1,4]benzodiazepin–2(1H)–thione (TIBO R82150)," *Mol. Pharmacol.*, 43: (1993) 11–16.

Mellors, J.W., "In vitro Selection and Molecular Characterization of Human Immunodeficiency Virus–1 Resistance to Non–Nucleoside Inhibitors of Reverse Transcriptase," *Mol. Pharmacol.*, (1991) 41: 446–451.

Mitsuya, H., et al., "Strategies for the Antiviral Therapy in AIDS," *Nature*, 325:773–778 (1987).

Myers, G., et al., "Retroviruses and AIDS 1991: A Compilation and Analysis of Nucleic Acid and Amino Acid Sequences," Theoretical Biology and Biophysic Group, Los Alamos National Laboratory, Los Almos, NM, p. II–22.

Nguyen, M.H., et al., "Resistance of Human Immunodeficiency Virus Type 1 to Acyclic 6–Phenylselenenyl– and 6–Phenylthiopyrimidines," *Antimicrob. Agents Chemother.* 38: (1994) 2409–2414.

Oberg, B., "Antiviral Effects of Phosphonoformate (PFA, foscarnet sodium)," *Pharmacol. Therap.*, 40: (1989) 213–85.

Oberg, B., "Antiviral Effects of Phosphonoformate (PFA, foscarnet sodium)," *Pharmacol. Therap.*, 19:387–415 (1983).

Oberg, B., et al., "Clinical Use of Foscarnet (Phosphonoformate)," In E. DeClercq (ed.) *Clinical Use of Antiviral Drugs*, pp. 223–240 Martinus Nijhoff Publishing (1983).

Peden, K., et al., "The Characterization of Infectious Molecular Clones of HIV–$1_{LAI}$, HIV–$1_{MAL}$, and HIV–$1_{ELI}$: Changes in Growth Properties on Passage is Tissue Culture," *Virology* 185: (1991) 661–672.

Pepose, J.S., et al., "Acquired Immune deficiency Syndrom. Pathogenic Mechanisms of Ocular Disease," *Ophthalmology*, 92:472–484 (1985).

Prasad, V.R., et al, "Isolation and Characterization of a Dideoxyguanosine Triphosphate–Resistant Mutant of Human Immunodeficiency Virus Reverse Transcriptase," *Proc. Natl. Acad. Sci. USA*, (1991) 88: 11363–11367.

Reddy M.M., et al., "Effect of Foscarnet Therapy on Human Immunodeficiency Virus p24 Antigen Levels in AIDS Patients with Cytomegalovirus Retinitis", *J. Infect. Dis.*, 166 (1992) 607–610.

Reed, L.J., et al., "A Simple Method for Estimating Fifty Percent End Points," *Am. J. Hyg.* 27:(1938) 493–496.

Richman, D.D., et al., "Nevirapine Resistance Mutations of Human Immunodeficiency Virus Type 1 Selected During Therapy," *J. Virol.* 68: (1994) 1660–1666.

Richman, D.D., et al., "The Toxicity of Azidothymidine (AZT) in the Treatment of Patients with AIDS and AIDS–Related Complex", *New Engl. J. Med.*, 317:192–197 (1987).

Ringden, O., et al., "Pharmacokinetics, Safety and Preliminary Clinical Experiences Using Foscarnet in the Treatment of Cytomegalovirus Infections in Bone Marrow and Renal Transplant Recipients," *J. Antimicrob. Chemother.*, 17:373–387 (1986).

Saag, M.S., et al., "Extensive Variation of Human Immunodeficiency Virus Type–1 in vivo," *Nature* 334: 440–444 (1988).

Safrin, S., et al., "Foscarnet–Resistant Herpes Simplex Virus Infection in Patient with AIDS," *J. Infect. Dis.*, 169: (1994) 193–196.

Safrin, S., et al., "Foscarnet Therapy in Five Patients with AIDS and Acyclovir–Resistant Varicella Zoster Virus Infection," *Ann. Intern. Med.*, 115: (1991) 19–21.

Sandstrom, E.,G., et al., "Inhibition of Human T–Cell Lymphotrophic Virus Type III in vitro by Phosphonoformate," *Lancet* i: 1480–1482 (1985).

Sandstrom, E.G, et al., "Antiviral Therapy in AIDS: Clinical Pharmacological Properties and Therapeutic Experience to Date," Review Article in *Drugs* 34:373–390 (1987).

Sarin, P.S., et al., "Inhibition of HTLV–III/LAV Replication by Foscarnet," *Biochem. Pharmacol.*, 34:4075–4079 (1985).

Schinazi, R.F., "Comparison of Inhibitory Activities of Various Antiretroviral Agents Against Particle–Derived and Recombinant Human Immunodeficiency Virus Type 1 Reverse Transcriptases," *Antimicrob. Agents Chemother.* 33: (1989) 115–117.

Schinazi, R.F., et al., "Delayed Treatment with Combinations of Antiviral Drugs in Mice Infected with Herpes Simplex Virus and Application of the Median–Effect Method of Analysis," *Antimicrob. Agents Chemother.*, 30:491–498 (1986).

Schinazi, R.F., "Strategies and Targets for Anti–Human Immunodeficiency Virus Type 1 Chemotherapy," pp. 126–143 In R.F. Schinazi and A. J. Nahmias (ed.) *AIDS in Children, Adolescents and Heterosexual Adults: An Interdisciplinary Approach to Prevention,* Elsevier, New York (1988).

Schinazi, R.F., et al., "Combinations of Isoprinosine and 3'–Azido–3'–Deoxythymidine in Human Immunodeficiency Virus Type 1 Infected Lymphocytes," *Antimicrob. Agents Chemoter.* 32:xxx–xxx (in press Dec. 1988).

Singer, D.R., et al., "Foscarnet for Cytomegalovirus Retinitis," *Ann. Intern. Med.* 103:962 (1985).

Spira, T.J., et al., "Micromethod for Assaying the Reverse Transcriptase of LAV–HTLV–III/Lymphadenopathy–Associated Virus," *J. Clin. Microbiol.* 25:97–99 (1987).

St. Jeor, S., et al., "Cytomegalovirus Replication in Cells Pretreated with 5'–Ido–2'–Deoxyuridine," *J. Viorl.* 11:986–990 (1973).

Studies of Ocular Complications of AIDS Research Group in Collaboration with the AIDS Clinical Trials Group, "Mortality in Patients with the Acquired Immunodeficiency Syndrome Treated with either Foscarnet or Ganciclovir for Cytomegalovirus Retinitis," *N. Engl. J. Med.,* 326: (1992) 213–220.

Sullivan, V., et al., "Isolation of Foscarnet–Resistant Human Cytomegalovirus: Patterns of Resistance and Sensibility to other Antiviral Drugs," *J Infect. Dis.* (1991) 164:781–4.

Surbone, A., et al., "Treatment of the Acquired Immunodeficiency Syndrome (AIDS) and AIDS–related Complex with a Regimen of 3'–Azido–2',3'–Dideoxythymidine (Azidothymidine or Zidovudine) and Acyclovir," *Ann. Intern. Med.,* 108:534–540 (1988).

Tachedjian, G., et al., "In Vitro Generation and Characterization of Foscarnet–Resistant HIV–1," *Abstracts of the Third International Workshop on HIV Drug Resistance,* Kauai, Hawaii, Aug. 2–5, 1994, p. 23 (1989).

Tachedijian, G., et al, "Foscarnet Therapy is not Associated with the emergence of Foscanet–Resistant Human Immunodeficiency Virus Type 1 in an Acquired Immunodeficiency Syndrome Patient," *J. Med. Virol.* 207–211.

Wahren, B., et al., "Reversible Inhibition of Cytomegalovirus Replication by Phosphonoformate," *Interviology* 14:7–15 (1980).

Walmsley, S.L., et al., "Treatment of Cytomegalovirus Retinitis with Trisodium Phosphonoformate Hexadydrate (Foscarnet)," *J. Infect. Dis.* 157:569–572 (1988).

Vrang, L., et al., "PPi Analogs as Inhibitors of Human T–lymphotropic Virus Type III Reverse Transcriptase," *Antimicrob. Agents Chemother.* 29:867–872 (1986).

Vrang, L., et al., "Inhibition of the Reverse Transcriptase from HIV by 3'–Azido–3'–Deoxythymidine Triphosphate and its Threo Analogue," *Antiviral Res.,* 7:139–149 (1989).

Yarchoan, R., et al., "Development of Antiretroviral Therapy for the Acquired Immunodeficiency Syndrom and Related Disorders," *New Engl. J. Med.* 316–557–564 (1987).

Yoshikawa, M., et al., "Studies of Phosphorylation.III Selection Phosphorylation of Unprotected Nucleosides," *Bull. Chem. Soc. Jap.* 42:3505–3508 (1989).

PHARMACEUTICAL COMPOSITION

This application is a continuation of application Ser. No. 08/033,852, filed Mar. 19, 1993, abandoned which is a continuation of application Ser. No. 07/764,983, filed Sep. 23, 1991, (Abandoned), which is a continuation of application Ser. No. 07/335,216, filed Apr. 7, 1989, (Abandoned).

The present invention relates to a new pharmaceutical composition comprising a combination of a first component which is 3'-azido-3'-deoxythymidine (AZT) or its 5'-triphosphate (AZT-TP), and a second component which is phosphonoformic acid or a therapeutically acceptable salt thereof (PFA). This new combination has been found to give synergistic antiviral effect against human immunodeficiency virus (HIV), especially HIV type 1 (HIV-1).

In a further aspect, the invention relates to a method for the treatment of HIV virus infection, especially HIV type 1 virus infections, and to a method for the treatment of AIDS by concomitant administration of AZT, or AZT/TP, and PFA.

The novel pharmaceutical combinations of AZT or AZT-TP and PFA will comprise the respective components at a ratio of from 1:200 to 1:8000, suitably from 1:1000 to 1:4000, given as ration AZT or AZT-TP to PFA on molar basis.

PFA is preferably used in the form of its tri-sodium salt. It was used in that form in the test described below.

In the tests described below, the HIV type 1 virus has been used. Combinations of 3'-azido-3'-deoxythymidine and phosphonoformate have been found to produce a moderate synergistic inhibitory effect against human immunodeficiency virus type 1 in vitro at concentrations that are easily achieved in humans. The synergistic effect was more pronounced with increasing concentrations and was not secondary to toxic effects of the drugs. 3'-Azido-3'-deoxythymidine neither inhibited the replication of human cytomegalovirus in human embryonic lung fibroblasts nor interfered with the anti-cytomegalovirus effect of phosphonoformate. Using partially purified reverse transcriptase of human immunodeficiency virus type 1 and human cytomegalovirus DNA polymerase, various combinations of 3'-azido-3'-deoxythymidine-5'-triphosphate and phosphonoformate produced strong indications of additive interactions. The synergistic interactions in infected cells and the additive effects observed at the reverse transcriptase level indicated that mechanisms other than the reverse transcriptase may be of importance for the inhibition of human immunodeficiency virus replication by these two compounds. A concomitant treatment of cytomegalovirus infections, such as cytomegalovirus retinitis, with phosphonoformate in AIDS patients receiving 3'-azido-3'-deoxythymidine may be appropriate and this combination may also be useful in controlling the infection with the human immunodeficiency virus.

Several reports have indicated that a number of agents can affect human immunodeficiency virus type 1 (HIV-1) replication in cell culture (4, 17, 23, 34, 45) 3'-Azido-3'-deoxythymidine (zidovudine, AZT), a modified nucleoside, has received considerable attention because it was the first agent shown in a multicenter, double-blind, placebo-controlled study to prolong life and provide clinical improvement in certain patients with AIDS and advanced AIDS-related complex who had been treated during a period up to six months (10). However, AZT is associated with pronounced toxicities which have limited its use in individuals with established AIDS (27, 40). Opportunistic infections of human cytomegalovirus (HCMV) is one of the major problems in individuals with AIDS. Cytomegalovirus retinitis has been described in approximately one third of this population (26). In the absence of therapy this infection inevitably leads to irreversible retinal necrosis and can progress to permanent blindness. Only two drugs, 9-(1,3-dihydroxy-2-propoxymethyl)guanine (ganciclovir, DHPG, 2'-NDG, or BIOLF-62) and phosphonoformate (foscavir, foscarnet, or PFA) have been investigated with some success as possible treatments against HCMV-infections (8, 20, 21, 25, 28, 36, 42). PFA, an analog of pyrophosphate, has the unique property of being effective against both HIV-1 and HCMV in vitro (5, 24, 30, 31, 41, 43). Recent observations by Jacobson et al. (19) have also demonstrated a significant reduction of HIV-1 p24 antigen concentrations in patients after a 14-day treatment with PFA. Since a concomitant treatment of PFA against CMV retinitis is currently being considered in HIV-infected individuals undergoing AZT therapy, it was important to determine the type of interaction produced by these drugs against HIV-1 and HCMV.

The use of combinations of compounds with different modes of action is an attractive and logical extension of any therapeutic approach to enhance drug efficacy. Lower doses of the drugs might be used, which also may reduce the potential toxicity caused by either drug alone and the appearance of drug-resistant virus. In fact, almost all of the currently available antiretroviral agents have been evaluated in combinations with AZT (4, 13, 34). For example, using a rigorous definition of synergy for drug interactions, Hartshorn et al. (15) demonstrated synergistic effects against HIV-1 in cell culture by combinations of PFA and recombinant alpha-A interferon. In a similar in vitro system, combinations of AZT and alpha-A interferon gl granulocyte-macrophage colony-stimulating factor (GM-CSF) have been reported to produce synergy (14, 16).

In this report, the effects of different combinations of AZT and PFA were examined on the replication of HIV-1 in human peripheral blood mononuclear (PBM) cells and HCMV Ad169 in human embryonic lung (HEL) fibroblasts. Since the major mode of action of PFA and the triphosphate derivative of AZT (AZT-TP) is an inhibition of the HIV-1 reverse transcriptase (RT) activity by different mechanisms (6, 7, 12, 43, 44), the effects of several combinations of the two compounds were also examined on the partially purified HIV-1 RT. For comparison, the effects of combinations of PFA and AZT-TP on the partially purified HCMV DNA polymerase were studied. (Parts of this work were presented at the Second International Conference on Antiviral Research in Williamsburg, Va., Apr. 10–14, 1988, and at the IV International Conference on AIDS in Stockholm, Sweden, Jun. 12–16, 1988).

MATERIALS AND METHODS

Compounds. PFA was provided by Astra ALab, Södertälje, Sweden. AZT and AZT-TP were synthesized and purified in our laboratory according to published methods (22, 44, 46). The purity of AZT and AZT-TP was established by reversed-phase and anion exchange HPLC methods and spectrophotometric analysis.

Cells, virus strains, and cell culture assays. PBM cells from healthy HIV-1 and hepatitis B virus seronegative donors were isolated and propagated as described previously (35). HIV-1 (strain LAV-1) was obtained from the Centers for Disease Control, Atlanta, and propagated in PHA-stimulated human PBM cells as described previously (35). The details of the methods used for infection and assaying the anti-HIV-1 effect in infected human PBM cells have been reported (35).

HCMV strain Ad169 was a gift from Dr. Fred Rapp, Hersey, Pa. Human embryonic lung (HEL) cells, obtained from the American Type Culture Collection, Rockville, Md., were cultured in Dulbecco modified Eagle medium as decribed previously (39). Viable cells were conducted microscopically using a hemacytometer and the trypan blue exclusion method. Plaque reduction assays were performed in confluent monolayers of HEL cells in 6-well plates (Costar, Cambridge, Mass.) with 100 to 200 pfu of HCMV Ad169. After an adsorption period of 1 hour, unadsorbed virus was removed and the monolayers were overlaid with Dulbecco modified Eagle medium containing 0.75% Sea-Plaque agarose (FMC BioProducts, Rockland, Me.), 2% heat inactivated fetal calf serum, and the appropriate concentration of drug. The plates were incubated at 37° C. in a humidified atmosphere containing 5% $CO_2$ for 10 to 12 days. The monolayers were then fixed with 10% buffered Formalin (Fisher Scientific Co, Fair Lawn, N.J.), stained with crystal violet, and the number of plaques were counted.

Cell proliferation. The drugs alone and in combination were evaluated for their potential toxic effects on uninfected PHA-stimulated human PBM cells. Flasks were seeded so that the final cell concentration was $3 \times 10^5$ cells ml. The cells were cultured with and without drug for 6 days at which time aliquots were counted for cell viability by using the trypan blue exclusion method.

RT activity assay with disrupted virions. Six ml supernatant from each culture was clarified from cells at 300× g for 10 minutes. Virus particles were then pelleted from 5 ml samples at 40.000 rpm for 30 minutes using a Beckman 70.1 Ti rotor and suspended in 200 µl of virus disrupting buffer [50 mM Tris-HCl pH 7.8, 800 mM NaCl, 20% glycerol, 0.5 mM phenylmethyl sulfonyl fluoride (PMSF), and 0.5% Triton X-100].

The RT assays were performed at 37° C. in 96-well microtiter plates using methods described previously (35, 38). The results were expressed as dpm/ml of the originally clarified supernatant.

RT activity assay with partially purified enzyme. HIV-1 reverse transcriptase was isolated from detergent disrupted virions obtained from the cell-free supernantant of infected PHA-stimulated PBM cells. The enzyme was purified by passing the extract through ion-exchange chromatography columns as described previously (12). The enzyme was characterized as HIV-1 RT based on its specific requirements according to previous description (1, 18). The standard reaction mixture (100 µl) contained 100 mM Tris-HCl (pH 8.0), 50 mM KCl, 2 mM $MgCl_2$, 5 mM dithiothreitol 400 µg/ml bovine serum albumin, 0.05 U/ml (3.1 µg/ml) of $(rA)_n(dT)_{12-18}$, 1 µM [$^3$H] dTTP (spec. act. 18,000 cpm/pmol) and 10 µl of HIV-1 Rt. The reactions were incubated and processed as previously described (7).

CMV DNA Polymerase Assay. The partially purified HCMV-specific DNA polymerase was a generous gift from Dr. B. Wahren, National Bacteriological Laboratory, Stockholm. The procedure for the purification of HCMV DNA polymerase by sequential chromatographic steps on DEAE-cellulose (Whatman DE-52) and phosphocellulose (Whatman P-11) and the measurement of enzyme activity have been described previously (5).

Calculation of synergy. To determine whether synergistic, additive or antagonistic antiviral effects were achieved in virus-infected cell cultures treated with combinations of AZT and PFA, or in enzyme assays with combinations of AZT-TP and PFA, the multiple drug effect analysis developed by Chou and Talalay (2, 3) was used. Briefly, the method involves plotting of dose-effect curves for each compound alone and in combinations. It is essential to use a fixed ratio of the agents in multiply diluted combinations in order to use the median-effect equation: $f_a/f_u = (C/C_m)^m$. In this equation, C is the concentration, $f_a$ and $f_u$ are the fractions of the system which are affected and unaffected, respectively, by concentration C. $C_m$ is the concentration required for a 50% effect (analogous to $IC_{50}$ to $EC_{50}$ values), and m is a Hill-type coefficient signifying the sigmoidicity of the dose-effect curve. The slopes (m) of the dose-effect plots, obtained for the studied compounds, provided information as to whether the compounds are mutually exclusive (i.e. similar modes of action) or mutually non-exclusive (i.e. different modes of action). When the plots of both compounds and their combination were all parallel, the effects of the two compounds were mutually exclusive. The interaction between two compounds was determined by calculating the combination index (C.I.) with assumptions, where appropriate, of either mutually exclusive or non-exclusive interactions. When uncertainty existed as to whether the drugs acted in similar or independent manners, the determination of C.I.-values were calculated under each assumption and compared. Values of C.I.<1 indicated synergy, C.I.=1 indicated additive effects, and C.I.>1 indicated antagonism. A computer program obtained from Elsevier-Biosoft, Cambridge, U.K. was used for automatic analysis of all dose-effect data. Additional details on using this method have been reported previously (33).

RESULTS

Effects in HIV-1 infected and uninfected PBM cells. The effects of AZT and PFA, alone and in combinations, on the HIV-1 replication in human PBM cells (measured as RT activity of disrupted virions) are shown in Table 1. The supernatant of untreated virus-infected human PBM cells contained a mean RT activity of 772 kdpm/ml (equivalent to 11.8 pmoles of dTMP incorporated into acid-insoluble product). A concentration-dependent decrease in RT activity was observed in cultures treated with each compound alone and their combinations. A 50% reduction of HIV-1 replication [median effective concentration ($EC_{50}$)], was observed at 0.006 µM AZT and 22 µM PFA when the drugs were tested alone and at 3.5 µM and 8.5 µM when combinations of AZT and PFA were tested at ratios of 1:1,000 and 1:4,000, respectively. The ratios of AZT to PFA were selected according to the approximate ratio of their $EC_{50}$-values. The upper part of Table 2 summarizes the slopes, median effect values, and correlation coefficients obtained from the median-effect plots of AZT, PFA, and their combinations, respectively. The observed slope values (m) were greater than one for both compounds and their combinations in HIV-1 infected cells, which indicated a sigmoidal nature of the dose-effect curves rather than hyperbolic (m=1). This is in accordance to what is normally observed in more organized biological systems where the dose-effect relationships of inhibitors are frequently sigmoidal rather than hyperbolic (2). Since the median-effect plots of AZT, PFA, and their combinations were not parallel to each other in HIV-1 infected cells (data not shown), the exclusively of the combined effects could not be established. Therefore, the C.I.-values were calculated under both mutually exclusive and mutually non-exclusive assumptions. As shown in Table 2, the C.I.-values of both combinations giving a 50%, 70%, or 90% reduction of the HIV-1 replication were all less than one, which suggested synergistic effects. The computer-generated C.I.-values for $f_a$ -values ranging from 0.05 to 0.95 for the studied combinations of AZT and PFA are shown in FIG. 1. Both combinations produced similar synergistic effect patterns which were concentration-dependent and increased with increasing concentrations.

At a ratio of 1:4,000, the combination of AZT and PFA produced no toxicity greater than the agents alone to uninfected PHA-stimulated PBM cells; the highest combined concentration tested was 128.032 µM. PFA was not toxic to PBM cells when tested up to 640 µM (data not shown).

Effects on HIV-1 reverse transcriptase. The synergistic effect observed in HIV-1 infected PBM cells by combinations of AZT and PFA could be a consequence of the different mechanisms involved in inhibiting the RT activity. A combination of AZT-TP and PFA may, therefore, produce synergistic effects at the RT level. To study whether this hypothesis would hold true, the effects of several different combinations of AZT-TP and PFA were investigated using partially purified HIV-1 RT. FIG. 2 shows the median-effect plot for the inhibition of HIV-1 RT by AZT-TP, PFA, and a representative combinations of the two components at a molar ratio of 1:20. Both inhibitors followed first-order kinetics (i.e. m-values were close to 1) and from the parallel lines it was apparent hat AZT-TP and PFA were mutually exclusive inhibitors. The slopes, median-effect concentrations, and C.I.-values calculated for AZT-TP and PFA alone and in the four different combinations studied (1:20, 1:50, 1:100, and 1:200) against the HIV-1 RT are presented in the lower part of Table 2. In contrast to what was observed in HIV-1 infected cells, slope values closer to one were observed. The C.I.-values were found to be close to one for $f_a$-values at 0.50, 0.70, and 0.90, which strongly suggested that all studied combinations produced additive effects. The computer-generated calculation of C.I.-values for combinations of AZT-TP and PFA at ratios of 1:20 and 1:200 were found to be close to one over the entire range of $f_a$-values (FIG. 3).

Effect on HCMV plaque formation. To study whether AZT would interfer with the anti-HCMV effect of PFA, the effects of four appropriate combinations (1:1, 1:2, 1:5, and 1:10) of the two compounds on the multiplication of HCMV Ad169 in HEL fibroblasts were studied. Whereas AZT was found to be virtually without inhibitory effect even at concentrations up to 200 µM (data not shown), a dose-dependent inhibition was obtained for PFA with an $EC_{50}$-value of 34 µM (Table 3). Although AZT did not significantly inhibit HCMV multiplication, an $EC_{50}$-value of 383 µM was extrapolated (data not shown) in order to calculate the C.I.-values for the studied combinations. As shown in Table 3, the obtained C.I.-values indicated an additive effect for all combinations of AZT and PFA examined. Furthermore, the $EC_{50}$-values obtained indicated that the contribution of PFA in each combination caused the antiviral effect.

Effects on the HCMV DNA polymerase. Since AZT-TP and PFA are structurally different and presumably inhibit the HCMV DNA polymerase activity by different mechanisms, the interaction of the two drugs was investigated for four different combinations, at ratios 5:1, 10:1, 25:1, and 50:1. As summarized in the lower part of Table 3, AZT-TP was found to inhibit the HCMV DNA polymerase activity with an observed $EC_{50}$-value of 25 µM. For PFA the corresponding $EC_{50}$-value of 0.78 µM was more than 30 times lower. All combinations of AZT-TP and PFA produced C.I.-values close to one when the HCMV DNA polymerase activity was inhibited between 50% and 90%. This indicated that all combinations of the two compounds produced an additive effect also at the HCMV DNA polymerase level.

Table 1. Effects of AZT and PFA alone and in combinations at ratios 1:1,000 and 1:4,000 on HIV-1 replication in human PBM cells.

TABLE 1

Effects of AZT and PFA alone and in combination at ratios 1:1,000 and 1:4,000 on HIV-1 replication in human PBM cells.

| Treatment (drug ratio) | Concn. (µM) | RT activity (kdpm/ml)[a] | Inhibition (%) |
|---|---|---|---|
| AZT | 0.002 | 750 | 3.0 |
|  | 0.004 | 584 | 24.5 |
|  | 0.008 | 343 | 55.7 |
|  | 0.016 | 35.9 | 95.5 |
| PFA | 8 | 703 | 9.1 |
|  | 16 | 455 | 41.1 |
|  | 32 | 190 | 75.5 |
|  | 64 | 93.1 | 88.1 |
|  | 128 | 35.9 | 95.5 |
| AZT/PFA (1:1,000) | 0.001/1 | 797 | −3.1 |
|  | 0.002/2 | 668 | 13.6 |
|  | 0.004/4 | 247 | 68.1 |
|  | 0.008/8 | 68.4 | 91.3 |
| AZT/PFA (1:4,000) | 0.001/4 | 635 | 17.8 |
|  | 0.002/8 | 551 | 28.8 |
|  | 0.004/16 | 238 | 69.3 |
|  | 0.008/32 | 4.6 | 99.5 |

[a]The activity of uninfected PBM cells was 5,100 dpm/ml. All values are corrected for the mean value of the blanks (995 dpm). The mean value of RT activity ± S.D. of triplicate untreated HIV-infected cells was 772 ± 50.8 kdpm/ml.

TABLE 2

Median effective concentration and combinations index (C.I.) values for AZT (AZT-TP) and PFA alone and at different drug ratios against HIV-1 replication in human PBM cells and purified HIV-1 reverse transcriptase.

| Treatment (drug ratio) | Parameter[a] | | | C.I. at $F_a$[b] of | | |
|---|---|---|---|---|---|---|
|  | m ± SE | $EC_{50}$ (µM) | r | 0.50 | 0.70 | 0.90 |
| HIV-1 infected cells | | | | | | |
| AZT | 3.02 ± 0.27 | 0.006 | 0.99 | | | |
| PFA | 1.89 ± 0.17 | 22.0 | 0.99 | | | |
| AZT/PFA (1:1,000) | 3.03 ± 0.10 | 3.5 | 0.99 | 0.71 (0.80) | 0.68 (0.76) | 0.65 (0.71) |
| AZT/PFA (1:4,000) | 3.20 ± 0.90 | 8.5 | 0.93 | 0.72 (0.85) | 0.65 (0.76) | 0.56 (0.64) |
| HIV-1 reverse transcriptase | | | | | | |
| AZT-TP | 0.87 ± 0.03 | 0.003 | 1.00 | | | |
| PFA | 0.91 ± 0.03 | 0.14 | 1.00 | | | |

TABLE 2-continued

Median effective concentration and combinations index (C.I.) values for AZT (AZT-TP) and PFA alone and at different drug ratios against HIV-1 replication in human PBM cells and purified HIV-1 reverse transcriptase.

| Treatment (drug ratio) | Parameter[a] | | | C.I. at $F_a^b$ of | | |
|---|---|---|---|---|---|---|
| | m ± SE | $EC_{50}$ (µM) | r | 0.50 | 0.70 | 0.90 |
| AZT-TP/PFA (1:20) | 0.89 ± 0.04 | 0.043 | 0.99 | 0.98 | 0.97 | 0.96 |
| AZT-TP/PFA (1:50) | 0.92 ± 0.02 | 0.074 | 1.00 | 1.02 | 0.99 | 0.93 |
| AZT-TP/PFA (1:100) | 0.87 ± 0.02 | 0.084 | 1.00 | 0.89 | 0.91 | 0.95 |
| AZT-TP/PFA (1:200) | 0.92 ± 0.02 | 0.11 | 1.00 | 0.95 | 0.93 | 0.90 |

[a] m is the slope (SE-values are given when four or more concentrations have been used in the median effect plot), $EC_{50}$ is the median effective concentration, and r is the correlation coefficient, as determined from the median effect plot.
[b] C.I. < 1 indicates synergy, C.I. = 1 indicates additivity, and C.I. > 1 indicates antagonism (See Materials and Methods). $F_a$ is a component of the median effect equation referring to the fraction of the system affected (e.g., 0.50 means the C.I. at a 50% reduction of activity). C.I.-values for HIV-1 infected cells were determined under both mutually exclusive and mutually nonexclusive (numbers in paranthesis) assumptions.

TABLE 3

Median effective concentration and combinations index (C.I.) values for AZT (AZT-TP) and PFA alone and at different drug ratios against CMV plaque formation in human fibroblasts and purified CMV DNA polymerase.

| Treatment (drug ratio) | Parameter[a] | | | C.I. at $F_a^b$ of | | |
|---|---|---|---|---|---|---|
| | m ± SE | $EC_{50}$ (µM) | r | 0.50 | 0.70 | 0.90 |
| CMV infected cells | | | | | | |
| AZT | 5.95 | 383 | 0.97 | | | |
| PFA | 1.88 ± 0.10 | 34 | 1.00 | | | |
| AZT/PFA (1:1) | 2.16 ± 0.39 | 61 | 0.97 | 0.97 (1.04) | 0.94 (1.03) | 0.91 (1.03) |
| AZT/PFA (1:2) | 1.71 ± 0.32 | 41 | 0.95 | 0.82 (0.85) | 0.87 (0.91) | 0.97 (1.05) |
| AZT/PFA (1:5) | 2.65 ± 0.22 | 52 | 0.99 | 1.29 (1.32) | 1.14 (1.17) | 0.94 (0.97) |
| AZT/PFA (1:10) | 2.30 | 33 | 0.92 | 0.89 (0.90) | 0.82 (0.83) | 0.72 (0.74) |
| CMV DNA Polymerase | | | | | | |
| AZT-TP | 0.88 ± 0.09 | 25 | 0.99 | | | |
| PFA | 0.79 ± 0.02 | 0.78 | 1.00 | | | |
| AZT-TP/PFA (5:1) | 0.74 ± 0.05 | 3.4 | 0.99 | 0.84 | 0.92 | 1.07 |
| AZT-TP/PFA (10:1) | 0.70 ± 0.02 | 6.1 | 1.00 | 0.93 | 1.10 | 1.45 |
| AZT-TP/PFA (25:1) | 0.78 ± 0.03 | 11 | 1.00 | 0.93 | 1.00 | 1.13 |
| AZT-TP/PFA (50:1) | 0.87 ± 0.08 | 16 | 0.99 | 1.01 | 0.98 | 0.94 |

[a] m is the slope (SE-values are given when four or more concentrations have been used in the median effect plot), $EC_{50}$ is the median effective concentration, and r is the correlation coefficient, as determined from the median effect plot.
[b] C.I. < 1 indicates synergy, C.I. = 1 indicates additivity, and C.I. > 1 indicates antagonism (See Materials and Methods). $F_a$ is a component of the median effect equation referring to the fraction of the system affected (e.g., 0.50 means the C.I. at a 50% reduction of activity). C.I.-values for CMV-infected cells were determined under both mutually exclusive and mutually nonexclusive (numbers in paranthesis) assumptions.

DISCUSSION

Figure 1:
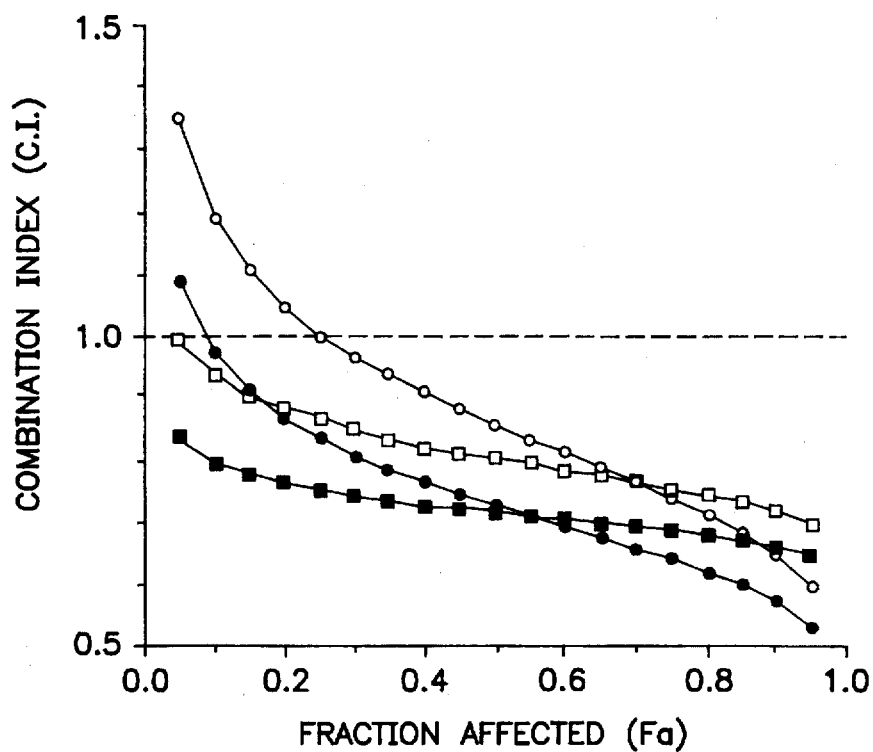
FIG. 1. Computer-generated graphical presentation of the combination index (C.I.) with respect to the fraction affected ($F_a$) for the inhibition of HIV-1 multiplication in human PBM cells. Combinations of AZT and PFA at ratios 1:1,000 and 1:4,000 were analyzed under both mutually exclusive [(-■-), (-●-)] and mutually non-exclusive [(-□-), (-○-)] assumptions, respectively.
Figure 3:
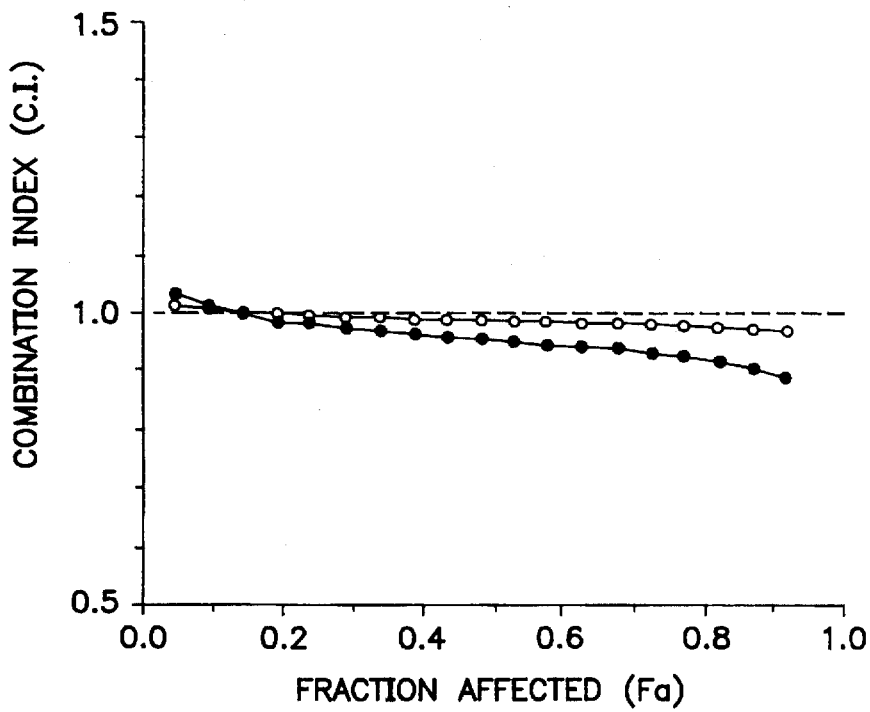
FIG. 3. Computer-generated presentation of C.I.-values versus $F_a$-values for combinations of AZT-TP and PFA at molar ratios of 1:20 (-○-) and 1:200 (-●-) against HIV-1 Rt. The C.I.-values were analyzed under mutually exclusive assumptions.
Figure 2:
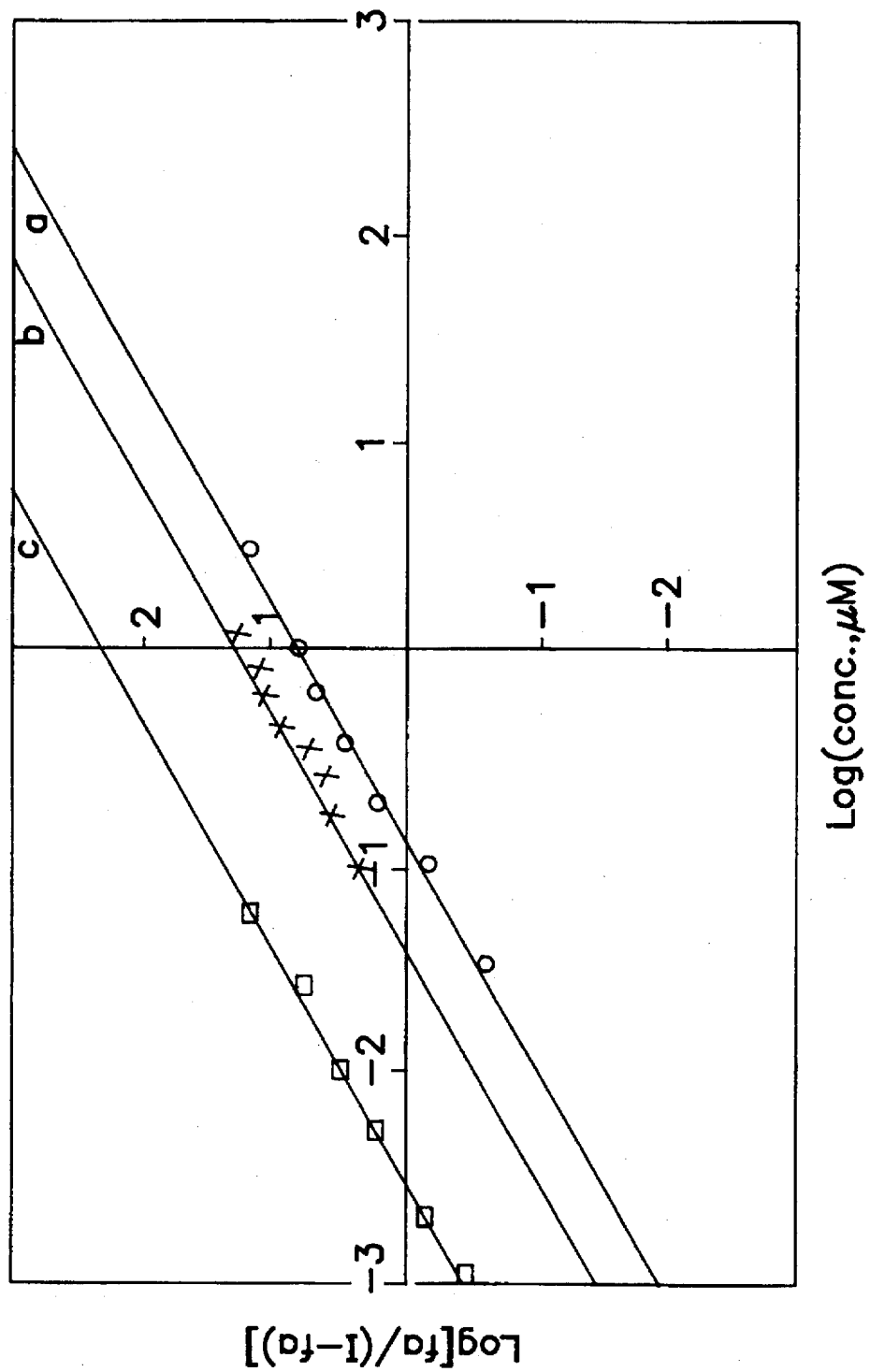
FIG. 2. Median effect plots for the inhibition of HIV-1 RT by AZT-TP (line c) and PFA (a) alone and a representative combination of the two compounds at a ratio of 1:20 (b). The slope values±S.E. were for AZT-TP 0.87±0.03, PFA 0.91±0.03, and the combination of 0.89±0.04.

An effective chemotherapeutic treatment of HIV-1 infections is a formidable challange. Not only does the virus infect and multiply in several different cells, it also establishes latency. A considerable genetic variability within and among clinical isolates has also been reported (9, 29). Since individual infected with HIV-1 will have to be treated for prolonged periods of time, drug-resistant variants of virus may be selected. A combination of chemotherapeutic agents may be used to enhance the distribution of drugs and their antiviral effects, decrease toxicity, reduce the potential risk of drug-resistance development, and, in the case of HIV-1- infections, both suppress virus-replication and help to restore the immune system. Since AZT has only a documented effect against HIV-1 infections, a concomitant therapy may be necessary to treat the opportunistic infections which occur in AIDS patients. Therefore, it was important to study to what extent PFA, a compound which not only has been shown effective against CMV retinitis, but also inhibits HIV replication, may interact with AZT against HIV-1 infections.

The results presented in this paper demonstrated that the interaction of AZT and PFA against HIV-1 replication in human PBM cells produced a moderate synergy, which was more pronounced with increasing $F_a$-values. In contrast, when combinations of AZT-TP and PFA were studied against HIV-1 RT activity, a clear additive effect was indicated. The latter result suggested that both drugs cannot simultaneously enter their binding sites on the enzyme and, therefore, the binding of and inhibition caused by one compound will prevent the other compound from exhibiting its antiviral effect. This so called mutually exclusive inhibition suggests that the binding sites for PFA and AZT-TP on the HIV-1 RT molecule may be overlapping. Mutually exclusive interactions have previously been observed for combination of 9-(2-hydroxyethoxymethyl)guanine (acyclovir, ACV) and PFA against herpesvirus DNA polymerase (11). The observed synergistic effect of AZT and PFA in HIV-1 infected cells and additive effect of AZT-TP and PFA against HIV-1 RT activity indicated that mechanisms other than the HIV-1 RT may be of importance in the inhibition of HIV-1 multiplication by these two compounds. In these studies, the synergistic effect of AZT and PFA against HIV-1 was observed without any indication of increased toxicity to uninfected human PBM cells.

The observed lack of synergistic effects of combinations of AZT and PFA against HCMV replication in cell culture could be predicted since AZT was shown not to possess any anti-HCMV effect. The observed "additive effect" resulted merely from the contribution of increasing concentrations of PFA in each of the different mixtures tested. The $EC_{50}$-values for PFA against HCMV Ad169 replication in cell culture and the partially purified HCMV DNA polymerase were in agreement with previous observations (5, 41). Although no inhibitory effect could be observed for AZT in HCMV-infected cells, AZT-TP was shown to be a weak inhibitor of the HCMV DNA polymerase activity with an $EC_{50}$-value of 25 µM. The additive effect observed at the DNA polymerase level suggested that, in analogy to what was discussed above for HIV-1, RT, the binding sites for PFA and AZT-TP may be overlapping. However, since concentrations of AZT in the millimolar range would have to be administered to HCMV-infected cells in order to achieve a concentration of AZT-TP close to its $EC_{50}$-value against the HCMV DNA polymerase activity, this may explain why no effect for AZT could be demonstrated at the concentrations tested. An administration of such high levels of AZT in attempts to control a HCMV-infection will cause cell-toxic effects in vitro and will probably not be clinically meaningful because of possible side effects.

The results presented demonstrated that, at concentrations easily attained in vivo, combinations of AZT and PFA interacted synergistically in inhibiting HIV-1 replication in human PBM cells. Furthermore, AZT had no effect against HCMV-infections in cell culture and AZT (or AZT-TP) did not antagonize the anti-HCMV effect of PFA. Although laboratory data does not necessarily predict what will happen in humans, our results support not only the concomitant use of PFA in AZT-treated individuals suffering from CMV infections, such as CMV retinitis, but also the consideration of clinical trials with combinations of AZT and PFA in HIV-1-infected individuals.

LITERATURE CITED

1. Cheng, Y. -C., G. E. Dutschman, K. F. Bastow, M. G. Sarngadharan, and R. Y. C. Ting. 1987. Human immunodeficiency virus reverse transcriptase. General properties and its interactions with nucleoside triphosphate analogs. J. Biol. Chem. 262:2187–2189.
2. Chou, T. -C., and P. Talalay. 1984. Qualitative analysis of dose-effect relationships: the combined effects of multiple drugs or enzyme inhibitors. Adv. Enzyme Regul. 22:27–55.
3. Chou, T. -C., and P. Talalay. 1984. Generalized equations for the analysis of inhibitors of Michaelis-Menten and higher order kinetic systems with two or more mutually exclusive and non-exclusive inhibitors. Eur. J. Biochem. 115:207–216.
4. De Clercq, E. 1987. Perspectives for the chemotherapy of AIDS. Anticancer Res. 7:1023–1038.
5. Eriksson, B., B. Öberg, and B. Wahren. 1982. Pyrophosphate analogues as inhibitors of DNA polymerases of cytomegalovirus, herpes simplex virus, and cellular origin. Biochem. Biophys. Acta. 696:115–123.
6. Eriksson, B., G. Stening, and B. Öberg. 1982. Inhibition of reverse transcriptase activity of avian myeloblastosis virus by pyrophosphate analogues Antiviral Res. 2:81–95.
7. Eriksson, B., L. Vrang, H. Bazin, J. Chattopadhyaya, and B. Öberg. 1987. Different patterns of inhibition of avian myeloblastosis virus reverse transcriptase activity by 3'-azido-3'-deoxythymidine-5'-triphosphate and its threo isomer. Antimicrob. Agents Chemother. 31:600–604.
8. Farthing, C., M. G. Anderson, M. E. Ellis, B. G. Gazzard, and A. Chanas. 1987. Treatment of cytomegalovirus pneumonitis with foscarnet (trisodium phosphonoformate) in patients with AIDS. J. Med. Virol. 22:157–162.
9. Fischer A. G., B. Ensoli, D. Looney, A. Rose, R. C. Gallo, M. S. Saag, G. M. Shaw, B. H. Hahn, and F. Wong-Staal. 1988. Biologically diverse molecular variants within a single HIV-1 isolate. Nature. 334:444–447.
10. Fischl, M. A., D. D. Richman, M. H. Grieco, M. S. Gottlieb, P. A. Volberding, O. L. Laskin, J. M. Leedom, J. E. Groopman, D. Mildvan, R. T. Schooley, G. G. Jackson, D. T. Durack, D. King, and the AZT Collaborative Working Group. 1987. The efficacy of azidothymidine (AZT) in the treatment of patients with AIDS and AIDS-related complex. A double-blind, placebo-controlled trial. New Engl. J. Med. 317:185–191.
11. Frank, K. B. and Y. -C. Cheng. 1985. Mutually exclusive inhibition of herpesvirus DNA polymerase by aphidicolin, phosphonoformate, and acyclic nucleoside triphosphates. Antimicrob. Agents. Chemother. 27:445–448.
12. Furman, P. A., J. A. Fyfe, M. H. St. Clair, K. Weinhold, J. L. Rideout, G. A. Freeman, S. Nusinoff Lehrman, D. P. Bolognesi, S. Broder, H. Mitsuya, and D. W. Barry. 1986. Phosphorylation of 3'-azido-3'-deoxythymidine and selective interaction of the 5'-triphosphate with human immunodeficiency virus reverse transcriptase. Proc. Natl. Acad. Sci. USA. 83:8333–8337.
13. Hall, M. J. and I. B. Duncan. 1988. Antiviral drugs and interferon combinations, p. 29–84 In H. J. Field (ed.), Antiviral agents: The development and assessment of antiviral chemotherapy. Vol. II. CRC Press Inc., Boca Raton, Fla.
14. Hammer, S. H., and J. M. Gillis. 1987. Synergistic activity of granulocyte-macrophage colony-stimulating factor and 3'-azido-3'-deoxythymidine against human immunodeficiency virus in vitro. Antimicrob. Agents Chemother. 31:1046–1050.

15. Hartshorn, K. L., E. G. Sandström, D. Neumeyer, T. H. Paradis, T. -C. Chou, R. T. Schooley and M. S. Hirsch. 1986. Synergistic inhibition of human T-cell lymphotropic virus type III replication in vitro by phosphonoformate and recombinant alpha-A interferon. Antimicrob. Agents Chemother. 30:189–191.

16. Hartshorn, K. L., M. W. Vogt, T. -C. Chou, R. S. Blumberg, R. Byington, R. T. Schooley, and M. S. Hirsch. 1987. Synergistic inhibition of human immunodeficiency virus by azidothymidine and recombinant alpha-A interferon. Antimicrob. Agents Chemother. 31:168–172.

17. Hirsch, M. S., and J. C. Kaplan. 1987. Treatment of human immunodeficiency virus infection. Antimicrob. Agents Chemother. 31:839–843.

18. Hoffman, A. D., B. Banapour, and J. A. Levy. 1985. Characterization of the AIDS-associated retrovirus reverse transcriptase and optimal conditions for its detection in virions. Virology. 147:326–335.

19. Jacobson, M. A., S. Crowe, J. Levy, F. Aweeka, J. Gambertoglio, N. McManus, and J. Mills. 1988. Effect of foscarnet therapy on infection with human immunodeficiency virus in patients with AIDS. J. Infec. Dis. 158:862–865.

20. Klintmalm, G., B. Lönnqvist, B. Öberg, G. Gahrton, J. -O. Lernestedt, G. Lundgren, O. Ringden, K. Robert, B. Wahren and C. Groth. 1985. Intravenous foscarnet for the treatment of severe cytomegalovirus infection in allograft recipients. Scand. J. Infec. Dis. 17:157–163.

21. Laskin, O. L., D. M. Cederberg, J. Mills, J. E. Lawrence, D. Mildvan, S. A. Spector, and the ganciclovir study group. 1987. Ganciclovir for the treatment and suppression of serious infections caused by cytamegalovirus. Am. J. Med. 83:201–207.

22. Lin, T. -S., and W. H. Prusoff. 1978. Synthesis and biological activity of several amino analogues of thymidine. J. Med. Chem. 21:109–112

23. Mitsuya, H. and S. Broder. 1987. Strategies for the antiviral therapy in AIDS. Nature. 325:773–778.

24. Öberg, B. 1983. Antiviral effects of phosphonoformate (PFA, foscarnet sodium). Pharmacol. Ther. 19:387–415.

25. Öberg, B., S. Behrnetz, B. Eriksson, H. Jozwiak, A. Larsson, J. -O. Lernestedt, and V. Lindsö Aberg. 1988. Clinical use of foscarnet (phosphonoformate), p. 223–240. In E. DeClercq (ed.). Clinical use of antiviral drugs. Martinus Nijhoff Publishing.

26. Pepose J. S., G. N. Holland, M. S. Nestor, A. J. Cochran, and R. Y. Foos. 1985. Acquired immune deficiency syndrome. Pathogenic mechanisms of ocular disease. Ophthalmology 92:472–484.

27. Richman, D. D., M. A. Fischl, M. H. Grieco, M. S. Gottlieb, P. A. Volberding, O. L. Laskin, J. M. Leedom, J. E. Groopman, D. Mildvan, M. S. Hirsch, G. G. Jackson, D. T. Durack, S. Nusinoff Lehrman, and the AZT collaborative working group. 1987. The toxicity of azidothymidine (AZT) in the treatment of patients with AIDS and AIDS-related complex. New Engl. J. Med. 317:192–197.

28. Ringden, O., B. Lönnqvist, T. Paulin, J. Ahlmen, G. Klintmalm, B. Wahren, J. -O. Lernestedt. 1986. Pharmacokinetics, safety and preliminary clinical experiences using foscarnet in the treatment of cytomegalovirus infections in bone marrow and renal transplant recipients. J. Antimicrob. Chemother. 17:373–387.

29. Saag, M. S., B. H. Hahn, J. Gibbons, Y. Li, E. S. Parks, W. P. Parks, and G. M. Shaw. 1988. Extensive variation of human immunodeficiency virus type-1 in vivo. Nature. 344:440–444.

30. Sandström, E. G., R. E. Byington, J. C. Kaplan, and M. S. Hirsch. 1985. Inhibition of human T-cell lymphotropic virus type III in vitro phosphonoformate Lancet 1:1480–1482.

31. Sarin, P. S., Y. Taguchi, D. Sun, A. Thornton, R. C. Gallo, and B. Öberg. 1985. Inhibition of HTLV-III/LAV replication by foscarnet. Biochem. Pharmacol. 34:4075–4079.

33. Schinazi, R. F., T. -C. Chou, R. T. Scott, J. Yao, and A. J. Nahmias. 1986. Delayed treatment with combinations of antiviral drugs in mice infected with herpes simplex virus and application of the median-effect method of analysis. Antimicrob. Agents Chemother. 30:491–498.

34. Schinazi, R. F. 1988. Strategies and targets for antihuman immunodeficiency virus type 1 chemotherapy, p. 126–143. In R. F. Schinazi and A. J. Nahmias (ed.) AIDS in children, adolescents and heterosexual adults: an interdiciplinary approach to prevention. Elsevier, N.Y.

35. Schinazi, R. F., D. L. Cannon, B. H. Arnold, and D. Martino-Saltzman. 1988. Combinations of isoprinosine and 3'-azido-3'-deoxythymidine in human immunodeficiency virus type 1 infected lymphocytes. Antimicrob. Agents Chemother. 32:xxx—xxx. (in press Dec. 1988)

36. Singer, D. R. J., T. J. Fallon, W. E. Schulenburg, G. Williams, and J. Cohen. 1985. Foscarnet for cytomegalovirus retinitis. Ann. Intern. Med. 103:962.

38. Spira, T. J., L. H. Bozeman, R. C. Holman, D. T. Warfield, S. K. Phillips, and P. M. Feorino. 1987. Micromethod for assaying the reverse transcriptase of LAV-HTLV-III/lymphadenophathy-associated virus. J. Clin. Microbiol. 25:97–99.

39. St. Jeor, S., and F. Rapp. 1973. Cytomegalovirus replication in cells pretreated with 5'-iodo-2'-deoxyuridine. J. Virol. 11:986–990.

40. Surbone, A., R. Yarchoan, N. McAtee, M. R. Blum, M. Maha, J. -P. Allain, R. V. Thomas, H. Mitsuya, S. Nusinoff Lehrman, H. Kessler, C. E. Myers, and S. Broder. 1988. Treatment of the acquired immunodeficiency syndrome (AIDS) and AIDS-related complex with a regimen of 3'-azido-2',3'-dideoxythymidine (azidothymidine or zidovudine) and acyclovir. Ann. Intern. Med. 108:534–540.

41. Wahren, B. and B. Öberg. 1980. Reversible inhibition of cytomegalovirus replication by phosphonoformate. Intervirology 14:7–15.

42. Walmsley, S. L., E. Chew, S. E. Read, H. Vellend, I. Salit, A. Rachlis, and M. M. Fanning. 1988. Treatment of cytomegalovirus retinitis with trisodium phosphonoformate hexahydrate (Foscarnet). J. Infect. Dis. 157:569–572.

43. Vrang, L. and B. Öberg. 1986. PPi analogs as inhibitors of human T-lymphotropic virus type III reverse transcriptase. Antimicrob. Agents Chemother. 29:867–872.

44. Vrang, L., H. Bazin, G. Remaud, J. Chattopadhyaya, and B. Öberg. 1987. Inhibition of the reverse transcriptase from HIV by 3'-azido-3'-deoxythymidine triphosphate and its threo analogue. Antiviral Res. 7:139–149.

45. Yarchoan, R. and S. Broder. 1987. Development of antiretroviral therapy for the acquired immunodeficiency syndrome and related disorders. New Engl. J. Med. 316:557–564.

46. Yoshikawa, M., T. Kato, and T. Takenishi. 1969. Studies of phosphorylation. III. Selective phosphorylation of unprotected nucleosides. Bull. Chem. Soc. Jap. 42:3505–3508.

What is claimed is:

1. A pharmaceutical composition comprising a combination of a first component which is 3'-azido-3'- deoxythymidine (AZT) or its 5'-triphosphate (AZT-TP), and a second component which is phosphonoformic acid or a therapeutically acceptable salt thereof (PFA), and wherein the ratio on a molar basis of AZT or AZT-TP to PFA is in the range from 1:200 to 1:8000, to enhance drug efficacy.

2. A method for the treatment of patients with drug-resistant variants of HIV that includes administering an effective amount of 3'-azido-3'-deoxythymidine (AZT) or its triphosphate and an effective amount of phosphonoformic acid or a therapeutically acceptable salt thereof (PFA), to enhance drug efficacy.

3. A method according to claim 2 where the said components are administered at a ratio of from 1:200 to 1:8000, given as ratio on molar basis of AZT or AZT-TP to PFA.

* * * * *